US010531860B2

(12) United States Patent
Chaggares et al.

(10) Patent No.: US 10,531,860 B2
(45) Date of Patent: Jan. 14, 2020

(54) HIGH FREQUENCY ULTRASOUND TRANSDUCER AND METHOD FOR MANUFACTURE

(71) Applicant: FUJIFILM Sonosite, Inc., Bothell, WA (US)

(72) Inventors: Nicholas Christopher Chaggares, Whitby (CA); Oleg Ivanytskyy, Toronto (CA); Guofeng Pang, Ajax (CA); Robert J. Kolaja, Toronto (CA)

(73) Assignee: Fujifilm Sonosite, Inc., Bothell, WA (US)

( * ) Notice: Subject to any disclaimer, the term of this patent is extended or adjusted under 35 U.S.C. 154(b) by 508 days.

(21) Appl. No.: 15/359,593

(22) Filed: Nov. 22, 2016

(65) Prior Publication Data

US 2017/0144192 A1  May 25, 2017

Related U.S. Application Data

(60) Provisional application No. 62/260,213, filed on Nov. 25, 2015.

(51) Int. Cl.
*A61B 8/00* (2006.01)

(52) U.S. Cl.
CPC .................................. *A61B 8/4483* (2013.01)

(58) Field of Classification Search
USPC ........................................................ 367/140
See application file for complete search history.

(56) References Cited

U.S. PATENT DOCUMENTS

| 5,423,220 | A | 6/1995 | Finsterwald et al. |
| 6,278,224 | B1 | 8/2001 | Sawada et al. |
| 6,821,253 | B2 * | 11/2004 | Wakabayashi ........ B06B 1/0622 310/336 |
| 8,316,518 | B2 | 11/2012 | Lukacs et al. |
| 9,184,369 | B2 * | 11/2015 | Chaggares .......... H01L 41/0475 |
| 9,555,443 | B2 * | 1/2017 | Chaggares .......... H01L 41/0475 |
| 9,603,580 | B2 * | 3/2017 | Chaggares ............ B06B 1/0622 |
| 2003/0187356 | A1 | 10/2003 | Wakabayashi et al. |
| 2004/0122319 | A1 * | 6/2004 | Mehi ................... G01S 7/52034 600/443 |
| 2008/0015438 | A1 * | 1/2008 | Mehi ................... G01S 7/52034 600/447 |

(Continued)

FOREIGN PATENT DOCUMENTS

WO  2014190326 A1  11/2014

OTHER PUBLICATIONS

International Searching Authority, international Search Report and Written Opinion, PCT Patent Application PCT/US2016/063431, dated Mar. 10, 2017, 13 pages.

(Continued)

*Primary Examiner* — James R Hulka
(74) *Attorney, Agent, or Firm* — Baker Botts L.L.P.

(57) ABSTRACT

An ultrasound transducer has an array of transducer elements that are electrically coupled to electrical conductors. In one embodiment, the conductors are included in a flex circuit and engage a conductive surface formed on a number of outwardly extending ribs on a frame that holds the ultrasound array. In one embodiment, the flex circuit includes an alignment feature that engages a corresponding registration feature on the frame so that the traces on the flex circuit align with the ribs on the frame.

17 Claims, 14 Drawing Sheets

(56) References Cited

U.S. PATENT DOCUMENTS

| | | | |
|---|---|---|---|
| 2010/0156244 A1* | 6/2010 | Lukacs | B06B 1/0622 |
| | | | 310/335 |
| 2011/0021919 A1* | 1/2011 | Mehi | G01S 7/52034 |
| | | | 600/446 |
| 2011/0071396 A1 | 3/2011 | Sano et al. | |
| 2013/0140955 A1* | 6/2013 | Chaggares | H01L 41/0475 |
| | | | 310/334 |
| 2013/0207519 A1* | 8/2013 | Chaggares | B06B 1/0622 |
| | | | 310/335 |
| 2014/0336512 A1* | 11/2014 | Mehi | G01S 7/52034 |
| | | | 600/443 |
| 2014/0350407 A1* | 11/2014 | Chaggares | B06B 1/0622 |
| | | | 600/459 |
| 2015/0173625 A1* | 6/2015 | Chaggares | A61B 5/0095 |
| | | | 600/407 |
| 2016/0107193 A1* | 4/2016 | Chaggares | H01L 41/0475 |
| | | | 310/317 |
| 2016/0118572 A1* | 4/2016 | Lukacs | B06B 1/0622 |
| | | | 367/140 |
| 2017/0143297 A1* | 5/2017 | Chaggares | A61B 8/0891 |

OTHER PUBLICATIONS

Supplementary European Search Report dated Jun. 26, 2019 in EP Application No. 16869203.
Notice of Allowance dated Jul. 10, 2018 in Taiwan Application No. 105138792, 5 pages.

* cited by examiner

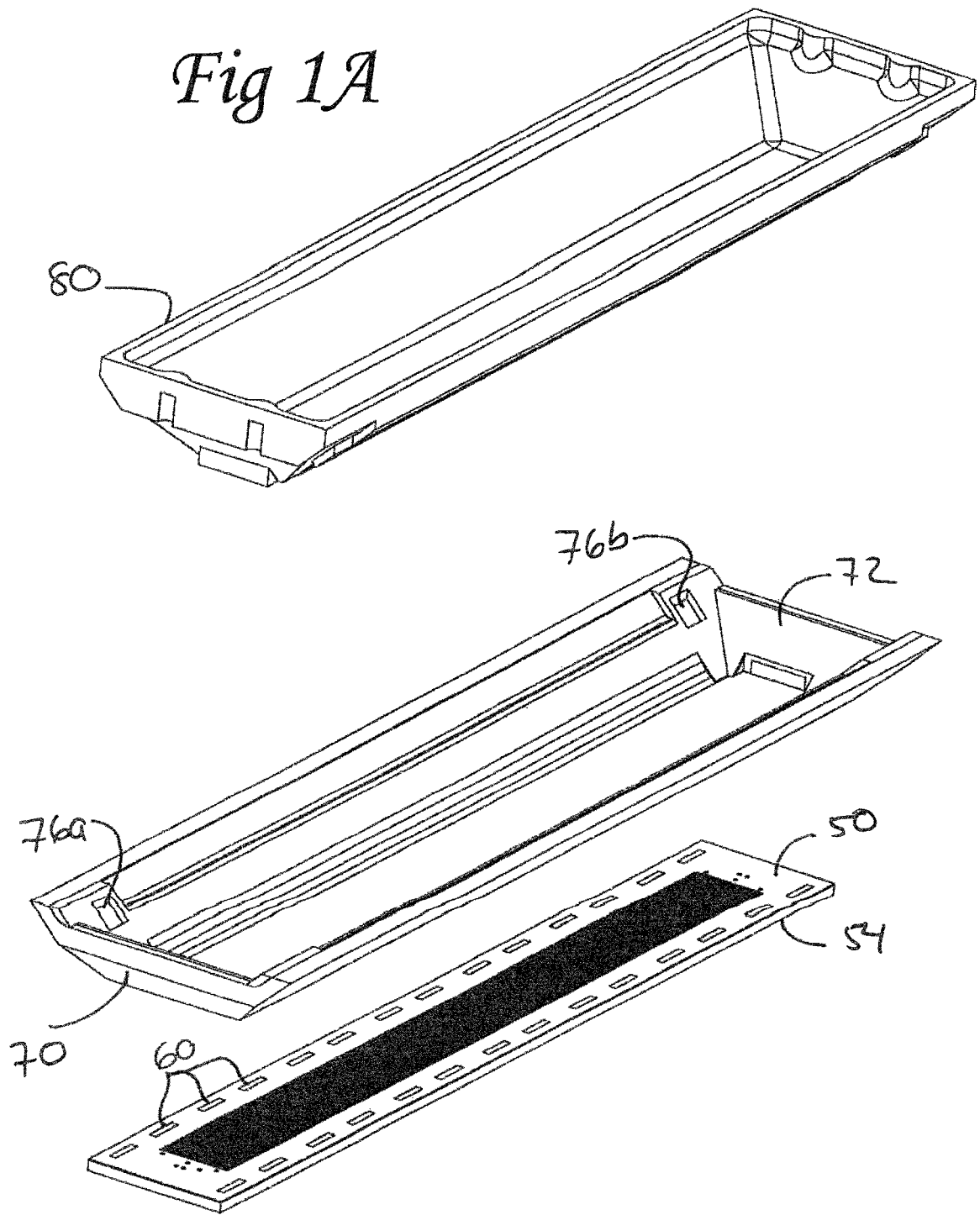

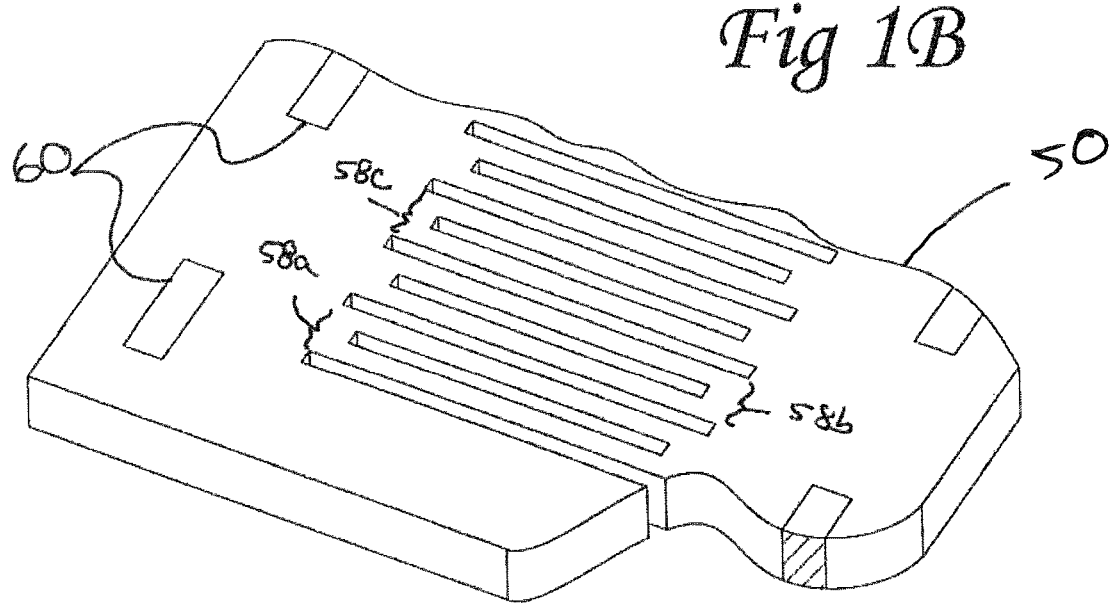

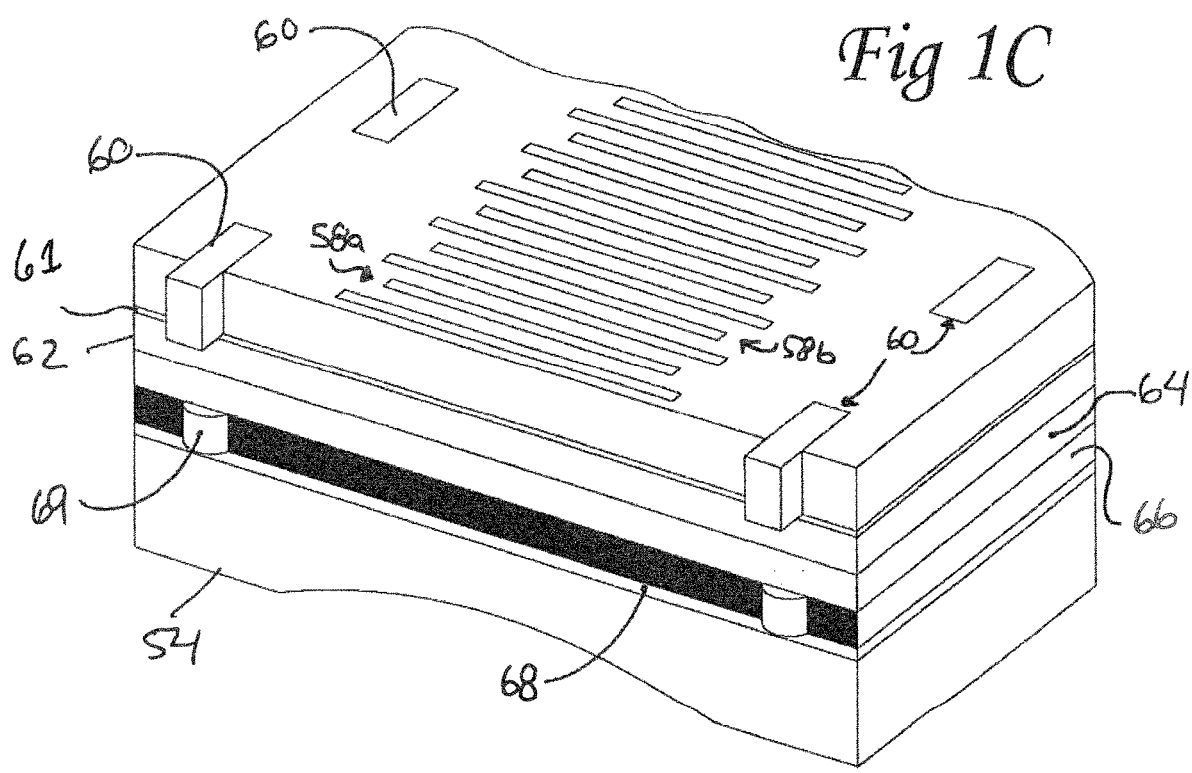

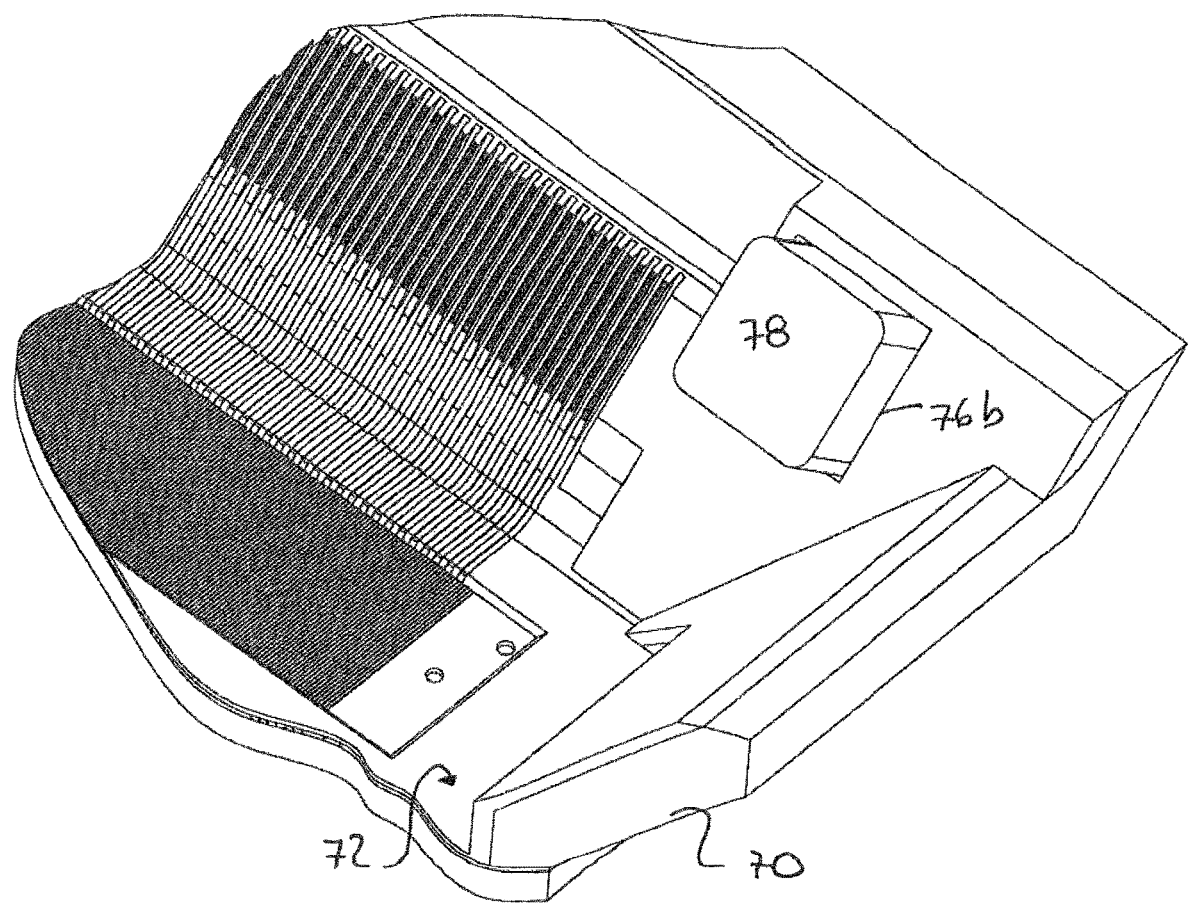

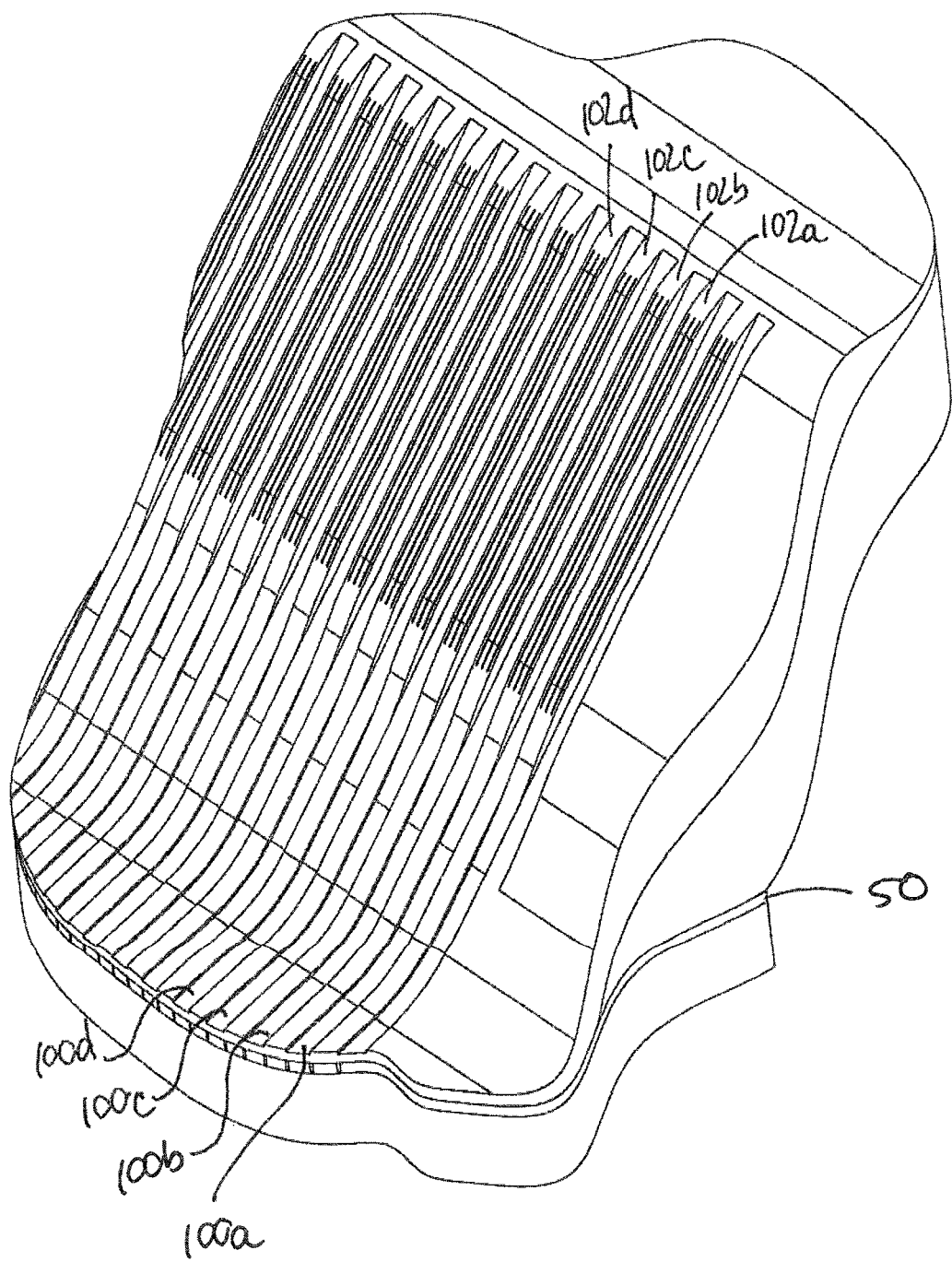

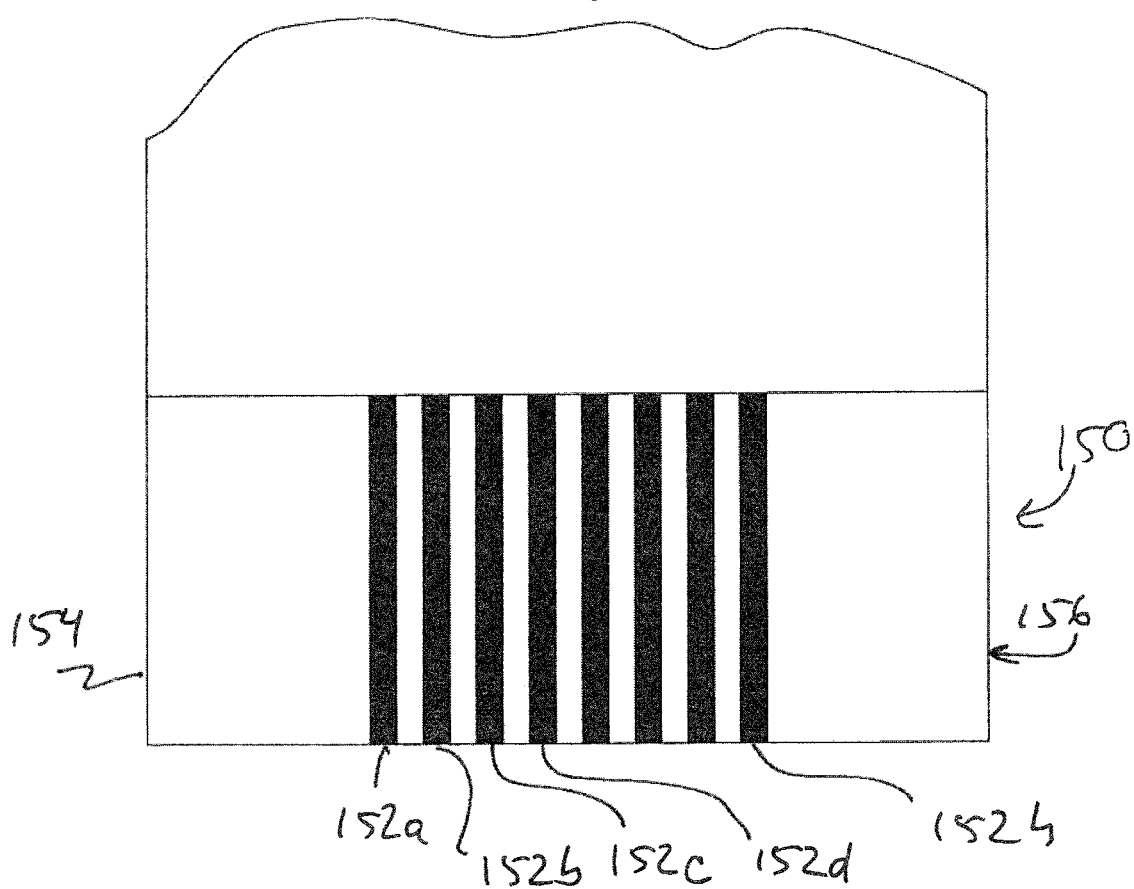

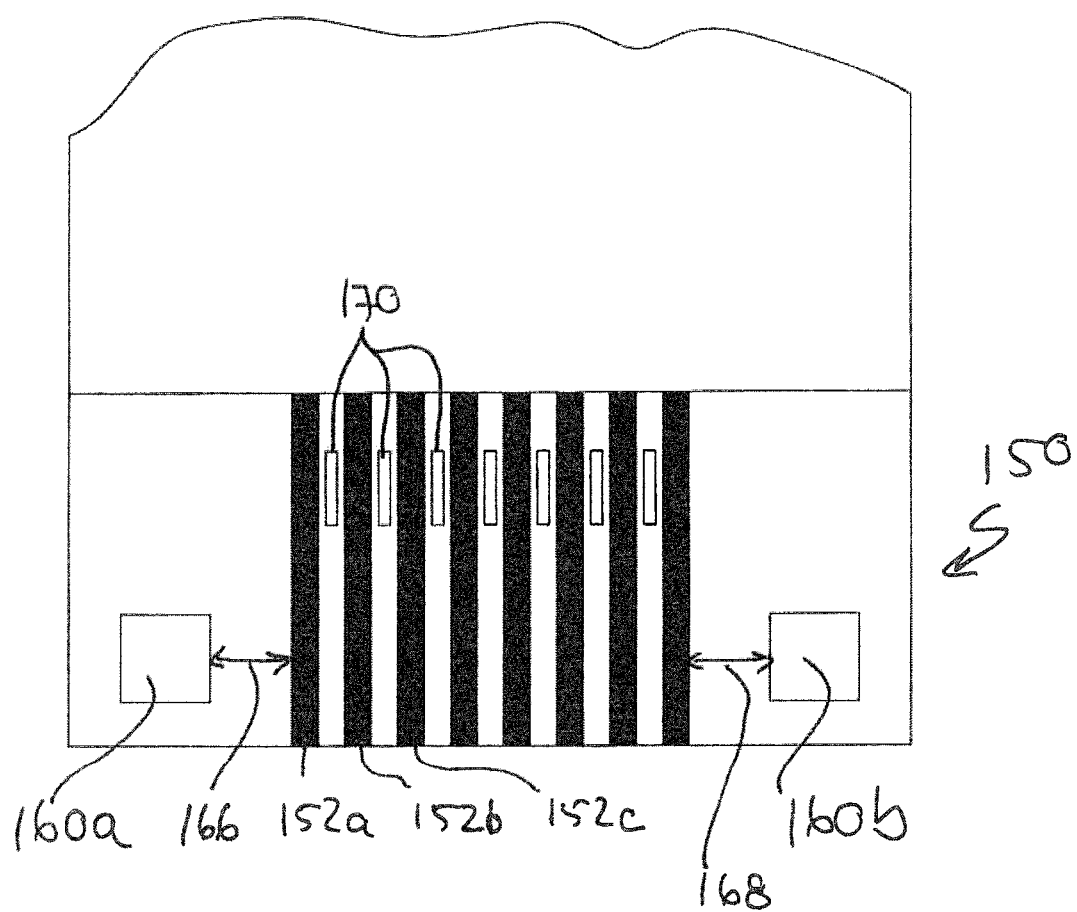

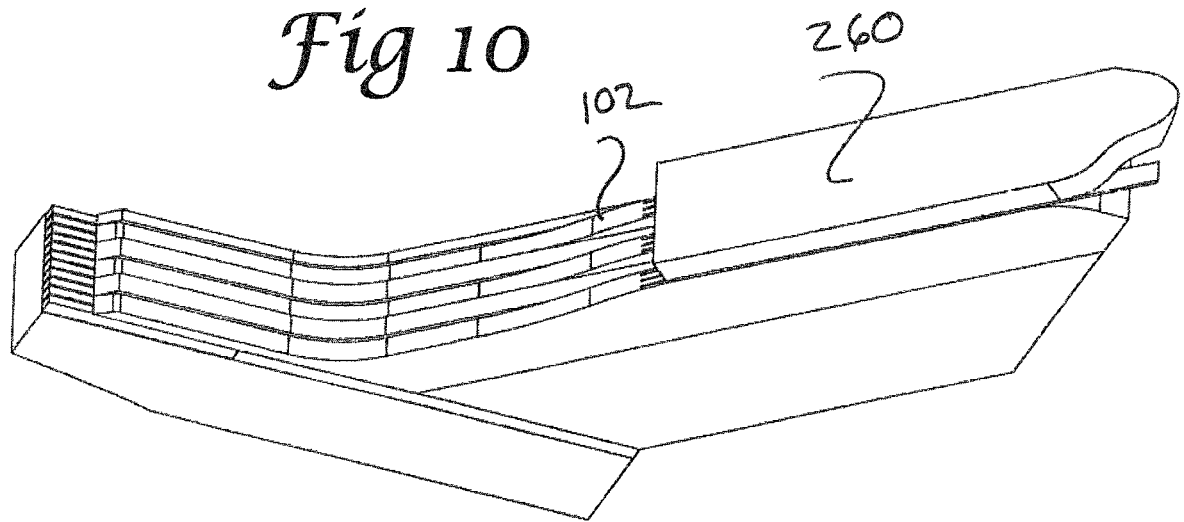

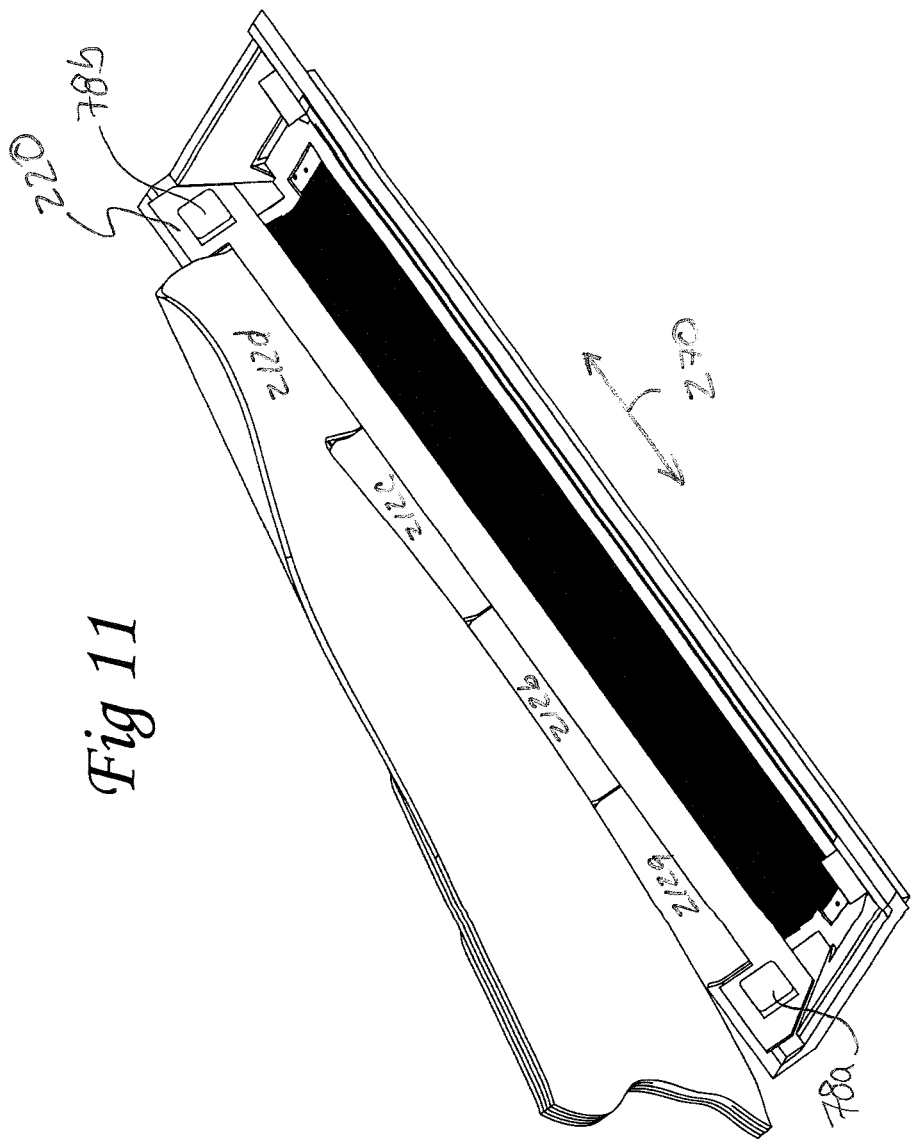

HIGH FREQUENCY ULTRASOUND TRANSDUCER AND METHOD FOR MANUFACTURE

RELATED APPLICATIONS

The present application claims the benefit of U.S. Provisional Application No. 62/260,213 filed Nov. 25, 2015, which is herein incorporated by reference in its entirety.

TECHNICAL FIELD

The disclosed technology relates to ultrasound transducers and in particular to methods of manufacturing high frequency ultrasound transducers.

BACKGROUND

In medical imaging or animal research applications, high frequency ultrasound is used to study the details of fine tissue structures and moving objects in a small area of interest. For example, in the field of cancer research, high frequency ultrasound is used to study the effects of drugs and other treatments on laboratory animals such as mice. Most diagnostic ultrasound systems utilize an array of 64, 128, 256 or more ultrasound transducer elements that are formed of a piezo-electric material. The transducer elements generate ultrasonic waves when excited with a voltage pulse and produce electronic signals when exposed to the corresponding echo signals.

As the frequency of the ultrasound systems increase, the sizes of individual transducer elements within an array decrease. For example, a 40 MHz transducer has a typical element pitch of 38-45 µM (microns), while a 60 MHz transducer has a typical element pitch of 25-30 microns. As a comparison, an average human hair has a diameter of approximately 80 microns. At this scale, one of the biggest challenges associated with manufacturing high frequency ultrasound transducers is connecting the leads that carry electrical signals to and from the elements of the transducer array. As will be understood by those of ordinary skill in the art, each transducer element must be electrically connected to a separate lead in order to allow a voltage signal to be placed across the element during signal transmission and to carry a voltage signal that is produced when the element is exposed to a returning ultrasonic echo signal. At these small dimensions, the challenge of aligning and bonding the individual electrical leads to the transducer elements is time consuming and prone to error.

Given these problems, there is a need for an improved method of creating a high frequency ultrasound transducer with electrical leads that are connected to individual transducer elements.

SUMMARY

As will be discussed in further detail below, the disclosed technology relates to an ultrasound transducer with an improved mechanism for bonding leads or traces to the individual transducer elements. In one embodiment, the transducer includes an array of transducer elements that is secured to a conductive frame. The frame is filled with a powder-filled epoxy, the epoxy forming a matrix suspending the powder uniformly therein, which powder-filled matrix is molded into a desired shape. The cured epoxy is then machined with a laser to create a series of channels that extend from individual transducer elements to a contact point on the frame where a circuit trace will be secured. Each channel transitions to an outwardly extending rib that rises above the surface of the epoxy in the frame. The channels and ribs are coated with an electrical conductor to create a conductive path from a rib to a corresponding transducer element. A pattern of conductive traces on a flex circuit is then aligned with the ribs on the frame so that each trace is electrically connected to a corresponding transducer element.

In one embodiment, registration features on the frame are used to align the traces of the flex circuit with the outwardly extending ribs. The flex circuit has one or more alignment features that cooperate with the registration features such that when the alignment features on the flex circuit are placed over the registration features on the frame, the conductive traces on the flex circuit align with the ribs on the frame.

BRIEF DESCRIPTION OF THE FIGURES

FIG. 1A illustrates an array of ultrasound transducer elements and a conductive frame in accordance with an embodiment of the disclosed technology;

FIG. 1B illustrates an array of transducer elements in a sheet of piezoelectric material in accordance with an embodiment of the disclosed technology;

FIG. 1C is an isometric, cross-sectional view of an array of transducer elements, a stack of matching layers and a lens element in accordance with an embodiment of the disclosed technology;

FIG. 2 shows a close up view of a corner of the conductive transducer frame and a registration feature in accordance with an embodiment of the disclosed technology;

FIG. 3 shows a close up view of a number of outwardly extending ribs formed on the frame that are configured to engage electrical traces on a flex circuit in accordance with an embodiment of the disclosed technology;

FIG. 4 shows a simplified flex circuit including a number of exposed traces;

FIG. 5 shows a flex circuit including a pair of alignment features that allow the traces to be aligned with conductors connected to the transducer elements in accordance with an embodiment of the disclosed technology;

FIG. 10 shows a flex circuit having traces that are electrically connected to a number of ribs on a frame in accordance an embodiment of the disclosed technology; and FIG. 11 shows a number of overlapping flex circuits having traces that are electrically connected to transducer elements and extend in a direction that is generally in-line with a length of the transducer array.

DETAILED DESCRIPTION

As discussed above, one of the challenges associated with manufacturing high frequency ultrasound transducers is performing the step of electrically connecting a number of conductive leads or traces to the individual transducer elements of a transducer array without disrupting the performance of the arrayed transducer elements. In the past, the conductive traces had to be aligned with the transducer elements by hand and then carefully handled until the fabrication process was completed. If the transducer assembly was accidently bumped or the traces were not correctly aligned, the result was a rejected part. This problem is even more acute as the operating frequency of the ultrasound transducer increases and the transducer elements become even smaller. The technology described herein simplifies the manufacturing process steps of aligning and connecting the conductive traces to the individual transducer elements of a transducer array.

Figure 1D:
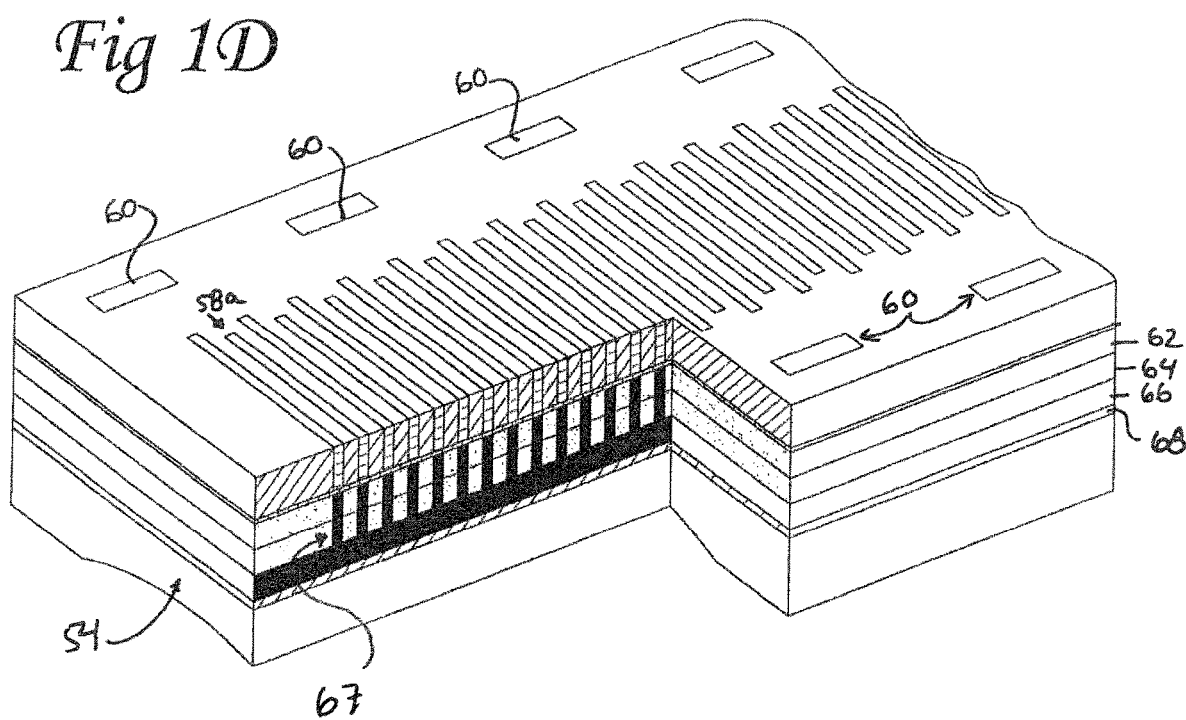
FIG. 1D is an isometric, cross-sectional view of an array of transducer elements in accordance with an embodiment of the disclosed technology.

FIGS. 1A-1D and the description below provide a brief overview of a number of steps performed when manufacturing a high frequency ultrasound transducer in accordance with some aspects of the disclosed technology. Additional details of some aspects of the manufacturing processes can be found in U.S. Patent Publication No's US 2013/0207519; US 2013/0140955; US 2014/0350407; and US 2015/0173625, all of which are commonly assigned to Fujifilm SonoSite Inc., the assignee of the present application and are herein incorporated by reference in their entirety. In one embodiment, a rectangular sheet of piezoelectric material 50 is mounted to a flat manufacturing puck with the lower surface facing up, and then machined with a patterning tool such as an excimer laser. The laser or other patterning tool is then used to create an array of individual transducer elements 58 in the sheet of piezoelectric material and to create a number of vias 60 that are spaced around the perimeter of the transducer array. As shown in FIG. 1B, an array includes a number of transducer elements 58a, 58b, 58c, and 58d etc. In one embodiment, each transducer element 58 is sub-diced in the center of each element along its length to prevent vibration in undesired modes. In the embodiment shown, the kerf slots that define the array elements and the sub-dices are shown having a length that is less than the width of the piezoelectric material. However, it is also possible to run the kerfs out to the edges of the piezoelectric material 50.

The spaces between the transducer elements and in the sub-diced kerf slots are filled with a suitable acoustically soft material such as, for example, a soft epoxy, using a vacuum pressure impregnation technique. After filling the kerfs, the surface is lapped or ground flat just to the surface of the piezoelectric material, and is then coated with a conductive material such as gold or chromium plus gold that forms a ground conductor on the lower surface of the transducer. The vias 60 are filled with a conductive epoxy covering and filling the plated via holes. With the vias now plated and filled, the vias 60 form electrically conductive paths to the conductor on front face of the transducer array. In operation, the conductor on the front face of the transducer is typically connected to an electrical ground while a driving signal is applied to the top of a selected transducer element by a conductive lead (not shown). When excited with the signal, the transducer element vibrates to produce an ultrasound acoustic signal. During a receive cycle, acoustic energy impinges on the transducer elements and creates signals on the lead that are read by signal processing circuitry (not shown)

As shown in FIGS. 1C and 1D, the front face of the transducer elements is connected to a lens material 54 through a number of matching layers. In one embodiment, two powder-filled epoxy matching layers 62 and 64 are applied to the conductor coated surface 61 of the piezoelectric material 50, each forming a part of a four layer matching layer system. Each of the layers 62 and 64 is lapped after it is applied to ensure the proper thickness of the layer.

A lens material 54 is then bonded to the outer surface of the matching layer 64. In one embodiment, the lens material 54 is a polymer such as Rexolite™ polystyrene. However, other lens materials could be used. In one embodiment, the lens material 54 is coated with a layer of adhesive such as cyanoacrylate (CA) glue 68, that is capable of adhering to the special lens material. The CA glue 68 can adhere to the lens surface and can be adhered to by other adhesives more generally useful for creating acoustic matching layers. The layer of cyanoacrylate glue 68 is lapped to a thickness suitable for acting as an acoustic matching layer at the frequency of the array, for example, a quarter wave matching layer. In one embodiment, the CA glued covered lens 54 is bonded to the matching layer 64 with a powder-filled epoxy adhesive 66. The adhesive 66 forms the third quarter wave matching layer of the 4-layer system, with the CA layer 68 forming the fourth of four layers. Before adhering the lens 54 to the matching layer 64, a series of kerfs 67 are created in the matching layers 62 and 64. As shown in FIG. 1D, the kerfs 67 are aligned with the spaces between the transducer elements 58.

The thickness of the adhesive 66 required to create the third matching layer is controlled by placing a number of spacing elements 69 around the lower perimeter of the sheet of piezoelectric material 50. The spacing elements 69 are lapped to a desired thickness to form pillars with a height that is selected so that the adhesive 66 forms the quarter wave matching layer. With the spacing elements 69 in place, the adhesive 66 is placed over the matching layers already applied to the surface of the piezoelectric sheet and the CA coated lens material 54 is pressed against the spacers 69 to bond the lens material 54 at the desired distance from the surface of the uppermost matching layer previously applied to the plated piezoelectric material 50. The adhesive 66, which is applied under vacuum, fills in the kerf slots 67 formed in the first and second matching layers 62, 64. In one embodiment, the composition of the matching layers 62, 64, 66 is described in commonly assigned U.S. Pat. Nos. 7,750, 536 and 8,343,289, which are herein incorporated by reference in their entirety.

The sheet of piezoelectric material 50, the acoustic matching layers, and the lens material 54 are then mounted lens side down to a manufacturing puck and lapped so that the transducer elements have a desired thickness.

A conductive metal frame 70 that is made of molybdenum or a like metal is bonded to the upper surface of the transducer array with a conductive epoxy. The conductive frame is therefore electrically connected to the conductive material on the front surface of the transducer through the paths created by the filled vias 60. The frame 70 has an open bottom surface so that an upper surface of the transducer elements is accessible through the opening in the bottom of the frame 70. The frame 70 has sloped side walls that together form a trough over the transducer array 58. In the embodiment shown, the frame is conductive to create an electrical path from the conductive surface on the distal side of the transducer through the vias. However, it is also possible to utilize a non-conductive frame and use a separate conductor such as a metal foil, wires or other conductor to electrically connect the conductive surface on the distal side of the transducer to the ground/shield layer of the flex circuit(s) containing the signal traces.

Once the frame 70 is bonded to the transducer array, a cover is placed over the transducer elements and a powder-filled epoxy 72 material is added to an open side of the frame 70. In one embodiment, the powder added to the matrix material is powdered silica that adds texture to the surface of the epoxy after laser machining. A mold 80 that is covered with a release agent is then pressed into the epoxy 72 while it cures to create a number of desired feature shapes in the frame. In one embodiment, the shapes include a pair of recesses 76a, 76b that are located on a sidewall of the frame at a location beyond the length of the ultrasound array. Additional recesses are formed on the opposite sidewall of the frame (not shown).

FIG. 2 shows a close up view of one corner of the frame 70 and a recess 76b that is formed in the epoxy 72. A registration feature 78 is placed in each of the recesses 76 and is used to align the electrical traces of a flex circuit to the transducer elements as will be described below. In one embodiment, the registration feature 78 is preferably made of molded powder-filled epoxy material and is precisely laser machined to a tolerance of for example, +/−5 microns. The registration features 78 can be secured within the recesses 76 with an adhesive. In some embodiments, an undersized recess 76 can be molded into the epoxy and trimmed to size with a laser or other micro-machining tool to accurately position the recess with respect to the position of the ribs (described below). With the recess accurately positioned and trimmed, a registration feature 78 is glued into the recess in order to fit with a corresponding alignment feature on the flex circuit. In some other embodiments, a blob of excess epoxy or the other glue can be placed on the frame and micro-machined with a laser or the like into a registration feature. The registration feature(s) on the frame and the corresponding alignment features on the flex circuits allow the exposed traces of the flex circuits to line up with the conductive ribs on the frame.

The powder-filled epoxy in the transducer frame 70 is then machined using the excimer laser to create a number of channels that connect to the individual transducer elements of the transducer array. As discussed in the patent applications mentioned above, the laser is used to create a pattern of channels that extend from a top surface of each transducer element and up a portion of a sidewall of the transducer frame. In the past, flex circuits were secured to the frame before the powder-filled epoxy was added to the frame in order to cover the exposed circuit traces with epoxy. A patterning tool such as the excimer laser would then be used to tunnel through the epoxy to expose a portion of a circuit trace on the flex circuit. While this worked well, the traces on the flex circuits were aligned with the transducer elements by hand before being fixed to the frame. In addition, the assembly was delicate until the transducer could be potted in a material that holds the flex circuits and transducer assembly together.

To improve on this assembly technique, one or more of the channels that connect each transducer element to a trace are fashioned so that each channel becomes a raised rib as it extends up the sidewall of the frame 70. As can be seen in FIG. 3, a number of channels 100a, 100b and 100c etc., are cut into the powder-filled epoxy 72 at a pitch that equals the pitch of every other transducer element (e.g. all the odd numbered transducer elements) while interleaving channels are created on the other side of the frame that are aligned with all the even numbered transducer elements. Alternatively, channels can be created on only one side of the frame 70 that align with each transducer element. In one embodiment, the channels that are aligned with each of the transducer elements have a depth that decreases as the channel extends outwardly from the transducer element. About half way up the sidewalls of the frame 70, the depth the channel is reduced to a point where the "channel" begins to extend outwardly from the surface of the epoxy to form an outwardly extending rib 102a, 102b and 102c etc. In one embodiment, the ribs 102 are created by ablating the powder-filled epoxy 72 on either side of the areas that define the ribs 102. In one embodiment, a number of score lines are created with the laser along the top surface of each rib to increase the surface area on top of the ribs 102 and to ensure robustness of the gold electrode during the pressing that takes place as part of the fixturing of the flex to the surface of the raised ribs.

Once the channels and the ribs and are patterned into the epoxy, the top surface of the transducer assembly is plated and processed to leave a conductive layer in the channels 100 and on top of the ribs 102. In one embodiment, the conductive material is applied by sputter coating a layer of metal such as gold or gold plus chromium on the surface of the transducer array including the top surface the transducer elements and the ribs. Next, a resist layer is applied over the transducer and exposed in areas where the conductive material is to be removed using photolithographic techniques. In one embodiment, the conductive material is to be removed from areas between the transducer elements, between the channel regions of the conductive paths, and should be removed from each side of the ribs. A chemical etch material is used to remove the conductive material where it is not wanted. Finally, a laser is used to remove any traces of conductive material that remain after the etch process.

After the laser-etch-laser (LEL) process, there is a conductive path created between the top surface of each transducer element and a corresponding rib 102 on the frame 70. A flex circuit with a number of exposed traces is then fixed to the frame so that the exposed traces align with corresponding ribs on the frame in order to create an electrical connection between the traces and the transducer elements. One of the benefits of this approach is that the flex circuits do not need to be secured to the transducer assembly while the top surface of the transducer is being coated with a conductive material. Therefore, there is less likelihood that the flex circuit connections will be broken during handling of the transducer. In addition, it is possible to fit more transducer assemblies into a sputtering machine chamber because the flex circuits are no longer attached while the coating is being applied. Therefore, more transducer assemblies can be processed at one time.

In the embodiment shown in FIG. 3, each of the ribs 102 terminates at the same height on the frame wall of the transducer. In another embodiment, the ribs 102 can terminate at different heights up the wall of the frame to allow interleaved traces to be connected to the ribs. For example, if the connections to be made to the transducer elements are smaller than the distance between the traces on a single flex circuit, the traces on two or more flex circuits can be staggered or interleaved. One set of traces e.g. traces 1, 3, 5 etc. can be placed in one layer of a flex circuit and traces 2, 4, 6 etc. can be placed in a different layer of the flex circuit that is set back from the exposed traces in the first layer. The exposed portions of the traces in each layer can be bonded to the ribs that extend to different heights on the wall of the transducer frame. A similar technique for interleaving traces is disclosed in published U.S. patent application US 2013-0140955 A1 referenced above, and incorporated by reference in its entirety.

Figure 9:
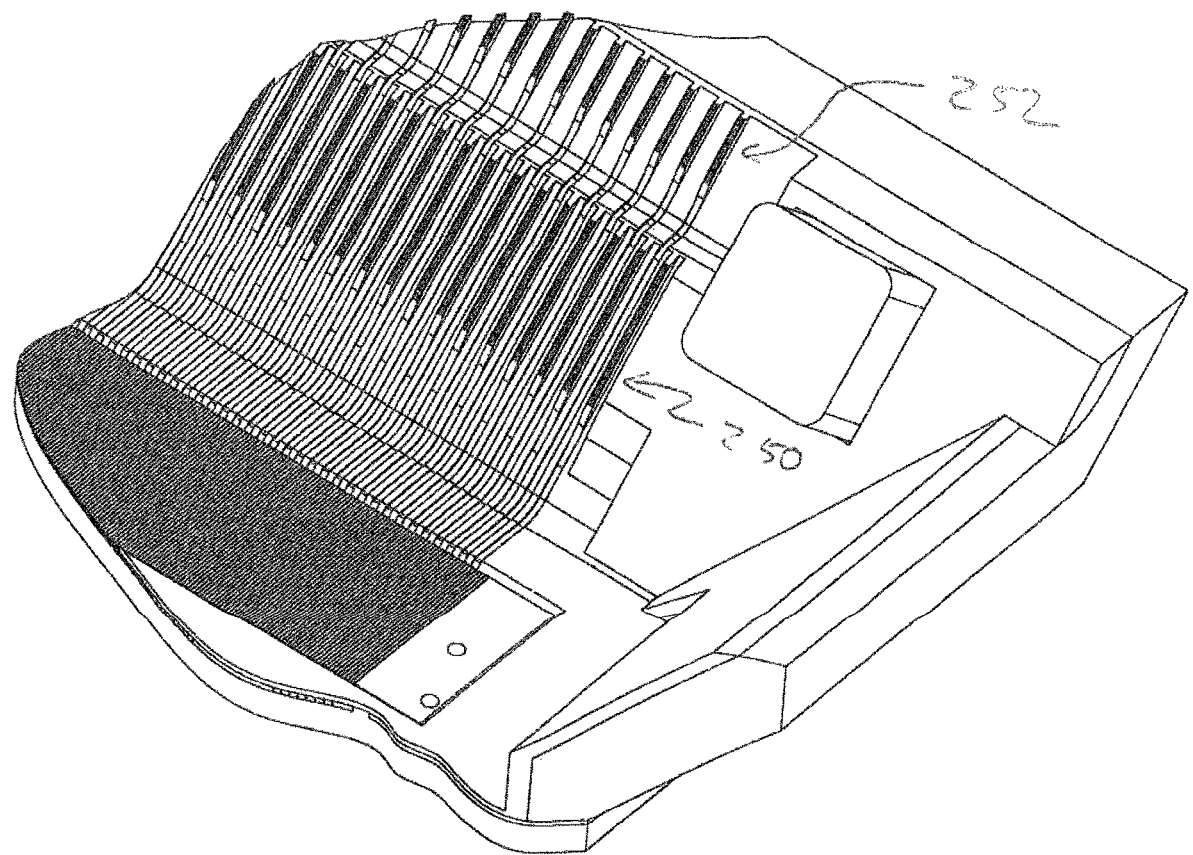
FIG. 9 shows a frame having interleaved ribs on two levels in accordance with another embodiment of the disclosed technology.

FIG. 9 shows an embodiment of a transducer having two sets of ribs at different levels. In the example shown, a frame includes a first set of ribs 250 at a first height on the frame wall and a second set of ribs 252 that extend higher up the frame. The ribs from each level are interleaved. One flex circuit (not shown) having exposed traces engages the ribs 252 while another flex circuit having exposed traces that engage the ribs 250. As will be appreciated, it is possible to have more than two layers of ribs formed in the epoxy material if desired.

In one embodiment, the exposed traces on the flex circuits are bonded to the ribs 102 with a non-conductive adhesive. Because the laser machined surface of the filled epoxy matrix is rough (on a microscopic scale) the coated particles of the matrix filler material on top of the ribs act as conductive spikes that pierce through the adhesive and engage the conductors of the flex circuit when the flex circuit and the ribs are bonded together. One or more ground connections of the flex circuit are connected to the metal frame 70 of the transducer assembly with a conductive epoxy.

Although manufacturers of flex circuits can create traces at a desired pitch with a high degree of accuracy, they often cannot control the distance between the edge of the flex circuit and the beginning of the traces with the same tolerances. There can be large variations in the distances between an edge of the flex circuit and a point where the traces begin. Therefore, it is not possible to simply align an edge of the flex circuit with a feature on the transducer frame and expect that the traces will align with conductors that are connected to the transducer elements. FIG. 4 shows a representative flex circuit 150 including a number of conductive traces 152a, 152b, 152c . . . 152h. The distances between the traces 152 are often very accurate. However, the distance between an edge 154 and the nearest trace 152a or between an edge 156 and the nearest trace 152h can vary significantly between different flex circuits. To address this problem, the registration feature 78 shown in FIG. 2 is used.

As shown in FIG. 5, one embodiment of the disclosed technology places alignment holes or features 160a, 160b in the flex circuit. Such features can be created with a laser at a predetermined distance 166, 168 from a reference point such as the nearest trace. As will be appreciated, the alignment holes 160 are designed to fit over the corresponding registration features 78 that are placed on or created in the frame 70. When the registration features 78 are placed in the alignment holes 160, the traces 152 on the flex circuit will align with the corresponding ribs 102 on the frame.

Figure 6:
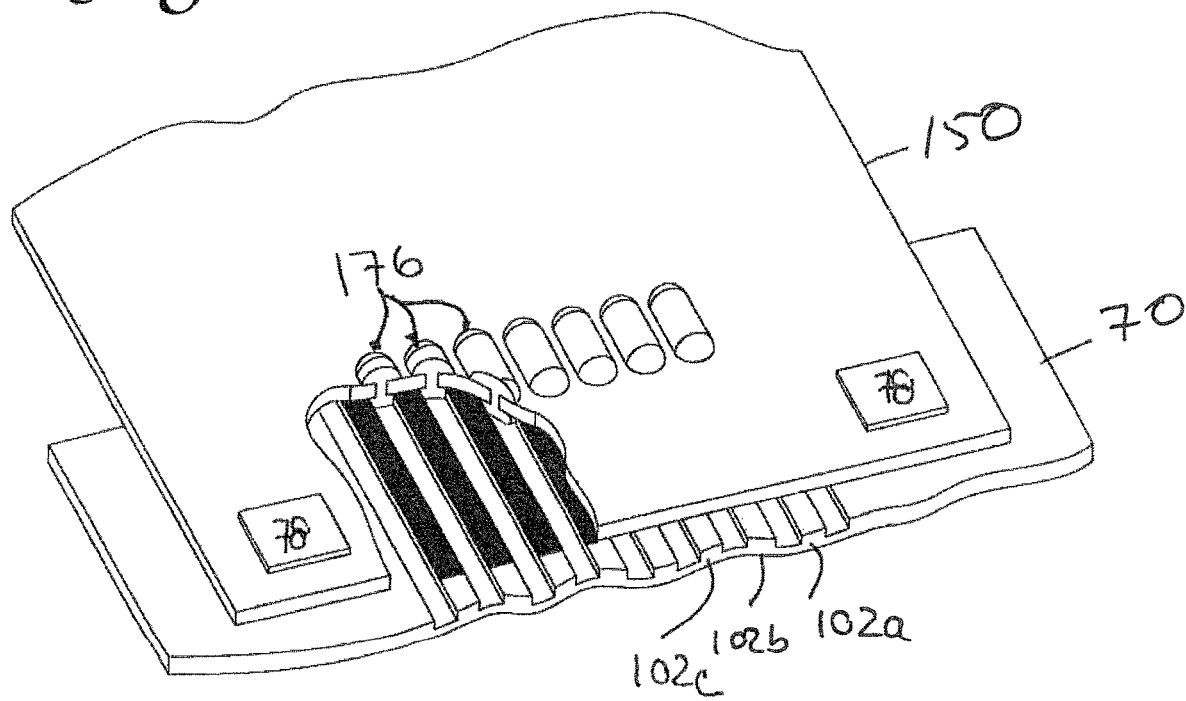
FIG. 6 shows a flex circuit placed over a number outwardly extending ribs in accordance with an embodiment of the disclosed technology.

In accordance with another aspect of the disclosed technology, some embodiments of the flex circuits include holes or vias 170 that are cut between the electrical traces 152. In one embodiment, the holes 170 are placed between each trace on the flex circuit. In another embodiment, the holes 170 are placed at other spaced intervals (or varying intervals) between the traces of the flex circuit. The holes 170 allow the adhesive that is used to secure the flex circuit to the ribs 102 to squeeze out and form rivet-shaped caps that help secure the flex circuit to the transducer frame. FIG. 6 shows an example of a flex circuit 150 that is secured to a number of ribs 102 on a frame 70. A portion of the adhesive that secures the flex circuit to the ribs on the frame is pressed through the holes 170 to form rivets 176 that help maintain the contact between the ribs and the traces and to help prevent the flex circuit from tearing off the frame 70.

FIG. 10 shows another example of how a flex circuit 260 having exposed traces (now shown) on its underside is secured to a number of conductive ribs 102 to electrically connect the traces in the flex circuit to the transducer elements. The conductive ribs face up and engage the downward facing exposed traces. The flex circuit 260 is held to the frame with an adhesive as described above.

In some embodiments, it is not possible or desirable to place all the traces that connect to the elements of the transducer array on a single flex circuit. One such example is medical device such as a prostate probe that includes a linear array of 512 transducer elements. In one embodiment, in order to reduce the size of a sleeve that carries the traces to the transducer elements, the traces are divided among four flex circuits that are stacked on top of each other. For example, one flex circuit has traces for the even numbered elements between element numbers 0-127, another has traces for the even numbered elements between element numbers 128-255, another has traces for the even numbered elements between element numbers 256-383 and another has traces for the even numbered elements between elements numbers 384-512. Another stack of four flex circuits is used to connect to the odd numbered transducer elements on the other side of the array. The two stacks of four flex circuits are then routed in a sleeve (not shown) that extends from the distal of the probe where the transducer is located to a connector at the proximal end of the probe.

Figure 7:
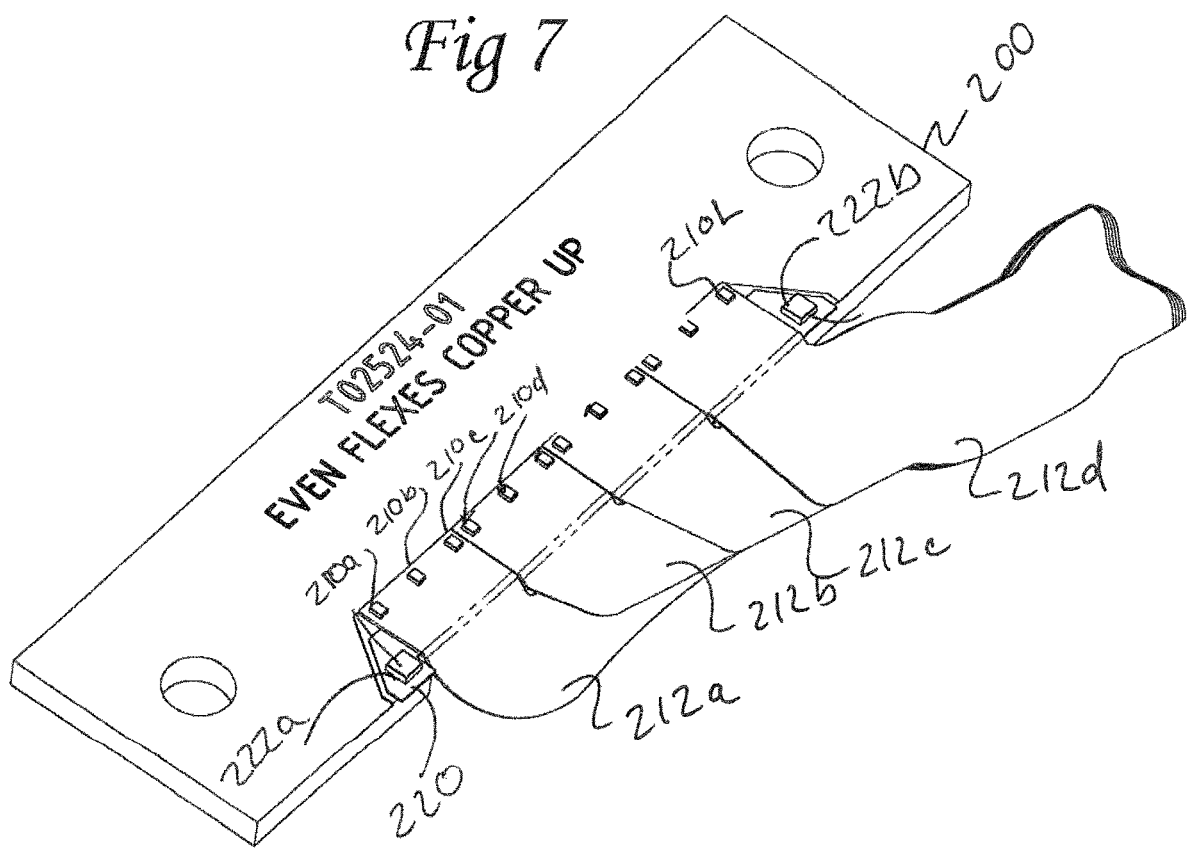
FIG. 7 shows a number of flex circuits placed in a jig with alignment features.

FIG. 7 illustrates one method of securing multiple flex circuits to a transducer array so that the traces on the flex circuits align with the ribs on the transducer frame. In the example shown, a number of flex circuits 212a, 212b, 212c and 212d are placed in a jig 200 that includes a number of tabs 210a, 210b . . . 210l formed therein. In one embodiment, the flex circuits are secured to a carrier bar 220 that is placed under the flex circuits. In one embodiment, the carrier bar 220 has at least one (and preferably two) alignment holes 222a, 222b that are sized to fit over corresponding registration features on the ultrasound frame. The sides of the flex circuits are trimmed so that adjacent traces on abutting flex circuits will keep the same pitch and holes or alignment features are created in the flex circuits 212 with a laser so that they fit over the tabs 210 when placed in the jig and the traces will be precisely aligned. When the holes on the flex circuits are placed over the tabs 210 in the jig 200, the traces on the flex circuits are positioned at known locations with respect to the holes 222a, 222b on the carrier bar 220. Once the flex circuits 212 are positioned on the tabs 210 and secured to the carrier bar 220, the excess flex circuit material in the area of the tabs 210 can be removed (e.g. with a laser) and the carrier bar 220 can be placed on the frame of the ultrasound transducer so that the alignment holes 222a, 222b fit over the registration features 78 on the frame. In the embodiment shown, the lengths of the flex circuits extending from the transducer array are stacked so that the traces in the flex circuits overlap each other vertically after turning away from the array support. However, the flex circuits could also extend in side by side manner to a connector if limiting the size of the connections to the transducer was not an important design concern.

Figure 8:
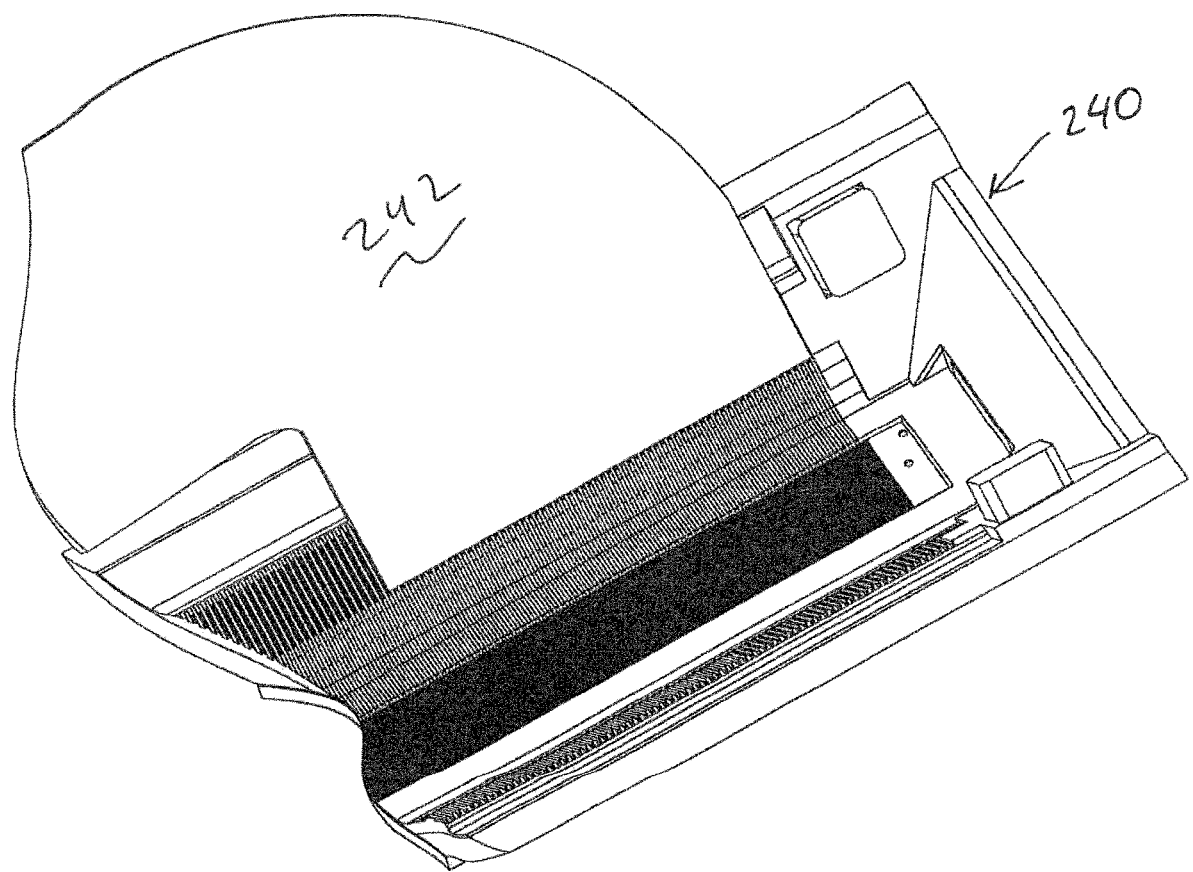
FIG. 8 shows an alternate embodiment of a flex circuit connected to a number of transducer elements in accordance with an embodiment of the disclosed technology.

FIG. 8 shows of a portion of a transducer 240 that may be used in a prostate probe or other medical device. In one embodiment, the transducer has 512 (or more) transducer elements. In order to make the probe as narrow as possible, a flex circuit 242 is angled so that the traces are in line with the transducer elements in the area of the transducer array but then turn 77 degrees (but could work for any angle) and then run in a direction that is aligned with the length of the transducer array. Additional flex circuits (not shown) are secured to the frame to carry signals from the other transducer elements. The lengths of the flex circuits are stacked vertically instead of side by side as they extend up a length of the probe so that the probe diameter can be made smaller.

FIG. 11 shows an example of a transducer assembly that includes of a number of flex circuits with traces that are electrically connected to individual transducer elements in an array. In the example shown, the transducer elements are electrically connected to traces in the flex circuits 212a, 212b, 212c and 212d that are positioned side by side along the length of the array in a direction 270. The alignment of the traces in the flex circuits is referenced by the position of the alignment holes 222a, 222b that are cut into the carrier bar. With the holes 222 in the carrier bar placed over the registration features 78a, 78b on the transducer frame, the traces in the flex circuits align with a corresponding rib on the transducer frame. In the embodiment shown, the flex circuits are positioned side by side to connect to the transducer elements but are arranged to stack on top of each other and to run in the direction 270 that is approximately in the long axis of the transducer array. This allows the connections to the transducer to be much more narrow than if the flex circuits were placed side by side. For an internal imaging probe, the reduction in the width of the flex circuits increases patient comfort. In the example shown, the flex circuits 212, 212b, 212c, 212d carry signals to and from the even (or odd) numbered transducer elements and a matching set of stacked flex circuits (not shown) on the other side of the transducer array are used to carry signals to and from the odd (or even) numbered transducer elements. In one embodiment, eight flex circuits having 64 traces each are used to carry signals to and from a 512 element transducer array. In one embodiment, a 512 element, side firing high frequency transducer array is useful in a prostate imaging probe.

From the foregoing, it will be appreciated that specific embodiments of the disclosed technology have been described herein for purposes of illustration, but that various modifications may be made without deviating from the scope of the invention. For example, it is not necessary that the registration features on the frame of the transducer and the flex circuit fit together as a post and a hole. Other shapes such as keys and keyways could be used. Alternatively, posts or other shapes could be secured at known locations on the flex circuit and holes or other shapes could be formed on the frame to align the flex circuits with the ribs on the frame. Accordingly, the invention is not limited except as by the appended claims.

We claim:

1. An ultrasound transducer comprising:
   a frame;
   an array of transducer elements secured to the frame;
   a number of conductive paths that connect to the transducer elements in the array, wherein the conductive paths include a rib along only a portion of the conductive paths, wherein the rib includes a conductive surface that extends outwardly from a surface of the frame and is configured to engage an electrical conductor; and
   one or more registration features that are positioned on the frame and configured to mate with an alignment feature on a flex circuit in order to align exposed traces in the flex circuit with the ribs of the conductive paths.

2. The ultrasound transducer of claim 1, wherein each rib is formed of an epoxy matrix material that is placed in the frame.

3. The ultrasound transducer of claim 2, wherein the epoxy matrix includes a filler material.

4. The ultrasound transducer of claim 3, wherein the filler material is silica.

5. The ultrasound transducer of claim 2, wherein each rib is aligned with a channel portion that is formed in an area adjacent a transducer element, wherein each channel has a depth that decreases to a point where the conductive path rises above the surface of the epoxy matrix material in the frame to become a rib.

6. The ultrasound transducer of claim 1, wherein each rib includes a number of scribe lines formed thereon that increase the surface area on a top of the rib.

7. The ultrasound transducer of claim 1, wherein each rib terminates at a same height on the frame of the ultrasound transducer.

8. The ultrasound transducer of claim 1, wherein ribs of the ultrasound transducer terminate at different heights on the frame of the ultrasound transducer.

9. An ultrasound transducer comprising:
   a conductive frame;
   an array of transducer elements having a bottom surface and a top surface that are formed in a sheet of piezoelectric material that is connected to the frame, and a lens material that is bonded to the bottom surface of the piezoelectric material; and
   a number of conductive paths that connect the top surface of the transducer elements to a circuit trace, wherein the conductive paths include an outwardly extending rib along only a portion of the conductive paths, wherein the rib is separated from a neighboring rib with a conductive surface by a space and are configured to engage an exposed circuit trace to carry signals to and from a corresponding transducer element.

10. The ultrasound transducer of claim 9, further comprising a flex circuit having a number of exposed traces therein, wherein the exposed traces of the flex circuit engage the ribs such that the traces are electrically connected through a conductive surface on top of a rib to a transducer element in the array.

11. The ultrasound transducer of claim 9, further comprising one or more registration features that are configured to engage corresponding alignment features on a flex circuit.

12. The ultrasound transducer of claim 10, wherein the flex circuit includes a number of holes placed between the traces in an area where the exposed traces engage the ribs, wherein the holes are configured to allow an adhesive to pass through the holes when the flex circuit is adhered to the ribs and form a number of rivet heads.

13. The ultrasound transducer of claim 9, further comprising a number of matching layers disposed between the bottom surface of the piezoelectric material and the lens, wherein the matching layers include a number of kerf slots that are cut into the matching layers and that are filled with an adhesive.

14. An ultrasound transducer comprising:
   a frame;
   an array of diced transducer elements that are formed in a sheet of piezoelectric material that is connected to the frame; and
   a number of conductive paths that connect to the transducer elements, wherein the conductive paths include an outwardly extending rib along only a portion of the conductive paths, wherein the rib is supported by the frame having and have a conductive surface that is configured to engage an exposed trace of a flex circuit; and
   one or more registration features on the frame that are configured to engage alignment features on the flex circuit to align exposed traces on the flex circuit with the ribs on the frame.

15. An ultrasound transducer comprising:
a frame;
an array of transducer elements that is secured to the frame;
a number of conductive paths that extend from the transducer elements, wherein the conductive paths include a raised rib along only a portion of the conductive paths, wherein the raised rib includes a conductive surface that is separated from an adjacent rib by a space; and
one or more flex circuits having an area of exposed conductive traces, wherein the exposed traces on the flex circuits are aligned with and electrically connected to a corresponding raised rib to electrically connect the trace to a transducer element in the array.

16. The ultrasound transducer of claim 15, wherein the transducer includes a number of flex circuits having exposed traces that are aligned side by side along a length of the array of transducer elements.

17. The ultrasound transducer of claim 16, wherein the number of flex circuits are stacked on top of each other at a position away from the transducer elements.

\* \* \* \* \*